US011951223B2

(12) United States Patent
Vu

(10) Patent No.: US 11,951,223 B2
(45) Date of Patent: Apr. 9, 2024

(54) METHOD AND APPARATUS FOR CLEANING, DISINFECTION, STERILIZATION, OR COMBINATIONS THEREOF

(71) Applicant: ASP Global Manufacturing GmbH, Schaffhausen (CH)

(72) Inventor: Roger Vu, Irvine, CA (US)

(73) Assignee: ASP Global Manufacturing GMBH (CH)

( * ) Notice: Subject to any disclaimer, the term of this patent is extended or adjusted under 35 U.S.C. 154(b) by 162 days.

(21) Appl. No.: 16/437,740

(22) Filed: Jun. 11, 2019

(65) Prior Publication Data

US 2020/0000951 A1 Jan. 2, 2020

Related U.S. Application Data

(60) Provisional application No. 62/692,268, filed on Jun. 29, 2018.

(51) Int. Cl.
*A61L 2/20* (2006.01)
*A61L 2/07* (2006.01)
*A61L 2/14* (2006.01)
*A61L 2/26* (2006.01)

(52) U.S. Cl.
CPC .............. *A61L 2/208* (2013.01); *A61L 2/07* (2013.01); *A61L 2/14* (2013.01); *A61L 2/26* (2013.01); *A61L 2/202* (2013.01); *A61L 2202/11* (2013.01)

(58) Field of Classification Search
None
See application file for complete search history.

(56) References Cited

U.S. PATENT DOCUMENTS

| 4,943,414 A * | 7/1990 | Jacobs | A61B 1/121 220/DIG. 7 |
| 5,008,106 A * | 4/1991 | Merianos | A61L 15/24 424/53 |

(Continued)

FOREIGN PATENT DOCUMENTS

| EP | 1308173 A1 | 5/2003 |
| EP | 2151183 A1 * | 2/2010 ......... A61B 1/00071 |

(Continued)

OTHER PUBLICATIONS

Engineering ToolBox (Water-Boiling Points at Vacuum Pressure), 2010, [online] https://www.engineeringtoolbox.com/water-evacuation-pressuretemperature-d_1686.html [Accessed May 13, 2021] (Year: 2010).*

(Continued)

*Primary Examiner* — Holly Kipouros
(74) *Attorney, Agent, or Firm* — Lerner David LLP

(57) ABSTRACT

A method and an apparatus are provided for cleaning, disinfecting, and/or sterilizing a device. The method comprises contacting an object with an obstructing substance such that the object is infiltrated with at least a portion of the obstructing substance. An absorptive and/or adsorptive capacity of the object is reduced by the obstructing substance. The object is contacted with a treatment agent after the capacity of the object is reduced. Infiltration of the object with the treatment agent is limited by the reduction of the capacity of the object.

24 Claims, 1 Drawing Sheet

(56) References Cited

U.S. PATENT DOCUMENTS

| | | | | |
|---|---|---|---|---|
| 5,667,753 | A | * | 9/1997 | Jacobs .................... C01B 15/08 422/23 |
| 6,010,662 | A | * | 1/2000 | Lin ........................ A61L 2/208 422/292 |
| 2001/0033807 | A1 | * | 10/2001 | Lin .......................... A61L 2/14 422/33 |
| 2002/0119074 | A1 | * | 8/2002 | McGowan, Jr. ........ A61L 2/206 422/26 |
| 2002/0160440 | A1 | | 10/2002 | McDonnell et al. |
| 2004/0081579 | A1 | * | 4/2004 | Bjerborn ............... B65B 55/103 422/28 |
| 2005/0042130 | A1 | * | 2/2005 | Lin ........................ A61L 2/208 422/33 |
| 2006/0008379 | A1 | * | 1/2006 | Mielnik .................. A61L 2/208 422/32 |
| 2009/0169424 | A1 | * | 7/2009 | Franchi .................... A61L 2/22 422/28 |
| 2016/0116449 | A1 | * | 4/2016 | Potas ...................... G01N 21/78 436/1 |
| 2017/0128982 | A1 | * | 5/2017 | Sheesley ................ B27K 5/003 |
| 2018/0221564 | A1 | * | 8/2018 | Patel ...................... A61L 2/081 |
| 2019/0192711 | A1 | * | 6/2019 | Fox, III ................. A61B 90/70 |

FOREIGN PATENT DOCUMENTS

| | | |
|---|---|---|
| WO | 2014020448 A2 | 2/2014 |
| WO | 2015143008 A2 | 9/2015 |

OTHER PUBLICATIONS

"Steam." Oed.com Oxford University Press, retrieved Aug. 25, 2021 (Year: 2021).*

"Steam." Merriam-Webster.com Merriam-Webster, retrieved Aug. 25, 2021 (Year: 2021).*

Trzaskowska et al., Pathogen reduction on mung bean reduction of *Escherichia coli* O157:H7, *Salmonella enterica* and *Listeria monocytogenes* on mung bean using combined thermal and chemical treatments with acetic acid and hydrogen peroxide, Published online Apr. 18, 2018, Food Microbiology (Year: 2018).*

Ukuku et al., Effect of Hydrogen Peroxide in Combination with Minimal Thermal Treatment for Reducing Bacterial Populations on Cantaloupe Rind Surfaces and Transfer to Fresh-Cut Pieces, 2016, Journal of Food Protection, vol. 79 No. 8, pp. 1316-1324 (Year: 2016).*

Yang et al., Preserving Cellulose Structure: Delignified Wood Fibers for Paper Structures of High Strength and Transparency, May 14, 2018, Biomacromolecules, 19, 3020-3029 (Year: 2018).*

International Search Report for International Patent Application No. PCT/IB2019/000778, dated Dec. 12, 2019.

Written Opinion for International Patent Application No. PCT/IB2019/000778, dated Dec. 12, 2019.

Sterrad, Advancing the quality of patient care, accessed at http://www.emea.aspjj.com/products-and-services/low-temperature-sterilization/sterrad-100nx-allclear, Mar. 1, 2018, 3 pages. Accessed Jun. 25, 2018.

McDonnell, et al., "Block's Disinfection, Sterilization, and Preservation", Sixth Edition, Sep. 21, 2020, Chapter 32, pp. 671-683.

* cited by examiner

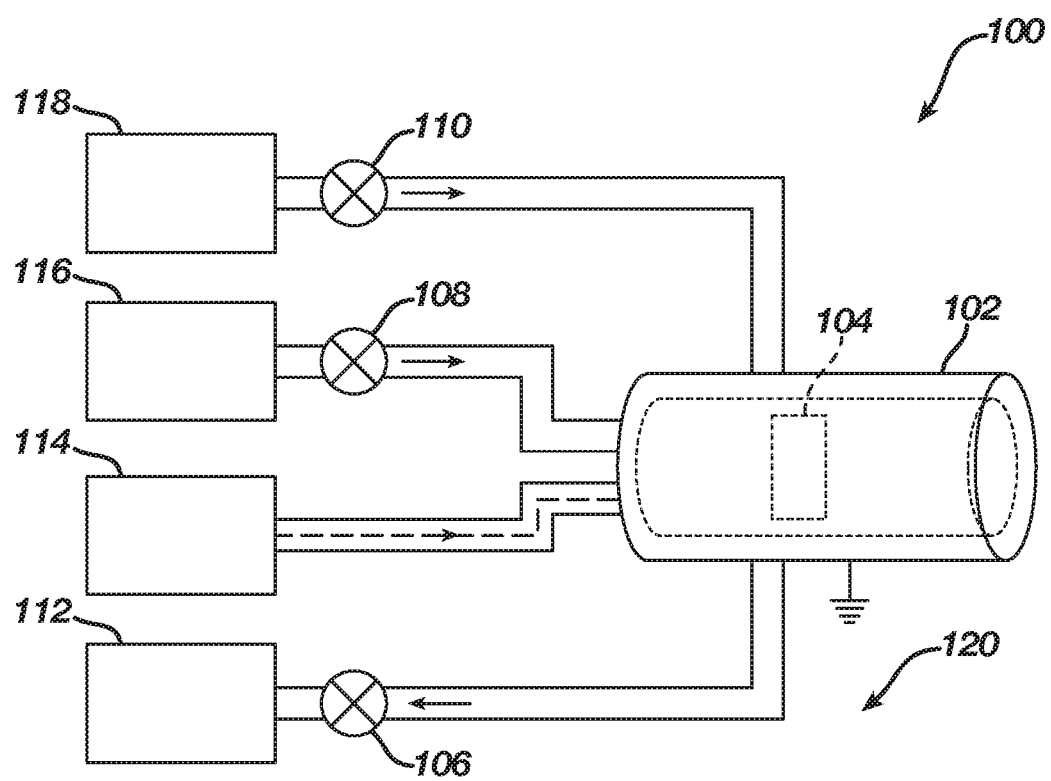

METHOD AND APPARATUS FOR CLEANING, DISINFECTION, STERILIZATION, OR COMBINATIONS THEREOF

CROSS REFERENCE TO RELATED APPLICATIONS

This application claims the benefit of U.S. Provisional Application No. 62/692,268 filed Jun. 29, 2018 which is hereby incorporated by reference.

FIELD

The present disclosure relates to a method and an apparatus for treating an object and reducing residuals on the object after the treatment.

BACKGROUND

Medical practitioners employ various medical devices during procedures on patients in the medical field. These devices are as varied as the procedures themselves. As such, proper care of these devices is critical for the proper corresponding treatment of the patient.

A critical aspect of the medical industry is the prevention of both cross-contamination and the spreading of disease. In this regard, treatment processes such as, for example, cleaning processes, disinfecting processes, and/or sterilization processes are used on medical devices and facility surfaces. These processes typically use heat, such as provided by steam, a chemical, such as hydrogen peroxide, irradiation, such as ultra-violet light, and/or pressure to treat the object.

SUMMARY

In one aspect, the present disclosure provides a method reduction of residuals. More specifically, the method comprises contacting an object with an obstructing substance such that the object is infiltrated with at least a portion of the obstructing substance. An absorptive and/or adsorptive capacity of the object is reduced by the obstructing substance. The object is contacted with a treatment agent after the absorptive and/or adsorptive capacity of the object is reduced. Infiltration of the object with the treatment agent is limited by the reduction of the absorptive and/or adsorptive capacity of the object.

In another aspect, the present disclosure provides a method reduction of residuals. More specifically, the method comprises contacting an object with a gaseous water composition such that the object is infiltrated with at least a portion of the gaseous water composition. An absorptive and/or adsorptive capacity of the object is reduced by the gaseous water composition. The object is contacted with a gaseous hydrogen peroxide composition after the absorptive and/or adsorptive capacity of the object is reduced and disinfected. Infiltration of the object with the gaseous hydrogen peroxide composition is limited by the reduction of the absorptive and/or adsorptive capacity of the object. At least a portion of the gaseous hydrogen peroxide composition is removed from the object. After the removal of the gaseous hydrogen peroxide composition from the object, a residual content of the gaseous hydrogen peroxide composition remaining on a surface of the object is less than or equal to 1,500 ppm/$cm^2$ by weight.

In another aspect, an apparatus reduction of residuals is provided. The apparatus comprises a chamber suitable to receive an object and a dispenser in fluid communication with the chamber. The dispenser is suitable to provide an obstructing substance and a treatment agent to the chamber. The chamber is suitable to facilitate infiltration of the obstructing substance into the object and is suitable to contact the object with the treatment agent after the infiltration of the at least portion of the obstructing substance. After removal of at least a portion of the treatment agent from the object, a residual content of the treatment agent remaining on the object is less than or equal to 1,500 ppm/$cm^2$ by weight.

It is understood that the inventions described in this specification are not limited to the examples summarized in this Summary. Various other aspects are described and exemplified herein.

BRIEF DESCRIPTION OF THE DRAWINGS

The features and advantages of the examples, and the manner of attaining them, will become more apparent and the examples will be better understood by reference to the following description of examples taken in conjunction with the accompanying drawings, wherein:

The FIGURE is a schematic view of an apparatus for reduction of residuals of an object according to the present disclosure.

Corresponding reference characters indicate corresponding parts throughout the several views. The exemplifications set out herein illustrate certain examples, in one form, and such exemplifications are not to be construed as limiting the scope of the examples in any manner.

DETAILED DESCRIPTION

Certain exemplary aspects of the present disclosure will now be described to provide an overall understanding of the principles of the structure, function, manufacture, and use of the devices and methods disclosed herein. One or more examples of these aspects are illustrated in the accompanying drawings. Those of ordinary skill in the art will understand that the devices and methods specifically described herein and illustrated in the accompanying drawings are non-limiting exemplary aspects and that the scope of the various examples of the present invention is defined solely by the claims. The features illustrated or described in connection with one exemplary aspect may be combined with the features of other aspects. Such modifications and variations are intended to be included within the scope of the present invention.

Reference throughout the specification to "various examples," "some examples," "one example," or "an example", or the like, means that a particular feature, structure, or characteristic described in connection with the example is included in at least one example. Thus, appearances of the phrases "in various examples," "in some examples," "in one example", or "in an example", or the like, in places throughout the specification are not necessarily all referring to the same example. Furthermore, the particular features, structures, or characteristics may be combined in any suitable manner in one or more examples. Thus, the particular features, structures, or characteristics illustrated or described in connection with one example may be combined, in whole or in part, with the features structures, or characteristics of one or more other examples without limitation. Such modifications and variations are intended to be included within the scope of the present examples.

In this specification, unless otherwise indicated, all numerical parameters are to be understood as being prefaced and modified in all instances by the term "about", in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Also, any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Any maximum numerical limitation recited in this specification is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification such that amending to expressly recite any such sub-ranges would comply with the requirements of 35 U.S.C. § 112 and 35 U.S.C. § 132(a).

An object can undergo a treatment process to prevent cross-contamination and the spread of disease. As used herein, a "treatment process" may be a cleaning process, a disinfecting process, a sterilization process, the like, and combinations thereof. A treatment process may be either manual, automated, or some combination thereof, and may utilize a treatment agent. As used herein, a "treatment agent" can comprise at least one of a cleaning agent, a disinfectant, and a sterilant. As used herein a "cleaning process" means a treatment process employing a cleaning agent that removes and/or eliminates debris such as, for example, a dirt, a dust, a particle, an oil, a protein, a carbohydrate, and the like. As used herein, a "cleaning agent" means a type of treatment agent that removes and/or eliminates debris during a cleaning process such as, for example, a surfactant and/or a detergent.

A disinfecting process and a sterilization process can remove and/or eliminate a bioburden from an object. A bioburden may be, for example, a bacterium (e.g., mycobacterium, bacterial spores), an archaeon, a eukaryote, a virus, a fungus, and/or other forms of biological agents. Bacterial spores (e.g., endospores) are a form of bacteria which are dormant and highly resistive to physical and chemical degradation. As used herein, a "disinfecting process" means a treatment process that substantially removes a bioburden except for bacterial spores. As used herein, "substantially remove" means that at least 99% of the bioburden has been removed from the object such as, for example, at least 99.9% of the bioburden, at least 99.99% of the bioburden, at least 99.999% of the bioburden, or at least 99.9999% of the bioburden has been removed from the object. As used herein, a "sterilization process" means a treatment process which substantially removes a bioburden including bacterial spores. The sterilization process may include, for example, the addition of heat, freezing, a sterilant, irradiation, pressure, and combinations thereof. The sterilant may comprise a chemical capable of sterilization. The disinfection process may include, for example, the addition of heat, a disinfectant, irradiation, pressure, and combinations thereof. The disinfectant may comprise a chemical capable of disinfection.

As used herein, the term "polymer" means prepolymers, oligomers, and both homopolymers and copolymers.

As used herein, a "mist" is meant to mean a substance comprising small droplets of liquid that are suspended in a gas. Mist can vaporize or evaporate into vapor. Mist may not condense, as mist is already in the liquid phase. Mist can be generated with a suitable liquid droplet generating device such as, for example, an ultrasound humidifier. Depending on the size and density of the small droplets of liquid, mist is generally visible to the naked eye.

As used herein, a "vapor" is meant to mean a substance in the gas phase that has a temperature lower than the critical temperature of the substance such that the vapor can be condensed to a liquid by increasing the pressure without reducing the temperature. Vapor can condense into a liquid phase from the gas phase. In various examples, water vapor is distinct from water mist.

A "gaseous composition" as used herein is meant to mean a liquid, a gas, or a combination thereof such as, for example, a vapor, a mist, a gas that has a temperature at least the critical temperature of the substance, or a combination thereof. For example, a gaseous water composition can comprise water vapor, a water mist, water gas, or combinations thereof.

Subjecting an object, such as a medical device, to a treatment process can occur in an treatment apparatus, such as a sterilizer. The sterilizer can comprise a sealable chamber into which the medical device can be placed. After the chamber is sealed, the pressure can be reduced by a pump and a treatment agent can be vaporized and dispensed into the sealable chamber, thereby contacting the medical device with the treatment agent. After a period of time has elapsed suitable to remove and/or eliminate bioburden the treatment agent can be removed. However, standard removal processes typically do not remove all of the treatment agent, and residual treatment agent may undesirably remain on the medical device.

Residual treatment agent, such as hydrogen peroxide, on the object may degrade the object and/or other surfaces the object comes into contact with. Minimizing residual treatment agent on medical devices can decrease the downtime of the medical device and can increase the operational life of the object. Thus, after the treatment process, the object may be subjected to additional processing to remove residual treatment agent. However, the additional processing step(s) typically require further time and resources that are in limited supply in medical facilities such as hospitals.

Accordingly, a treatment process is provided herein which can reduce the accumulation of residual treatment agent on an object by contacting the object with an obstructing substance which can infiltrate into the object before the treatment agent is applied. As used herein, "infiltrate" means that the obstructing substance penetrates and/or permeates the pores or interstices of at least the surface of the object and/or saturates the surface of the object. For example, infiltrate means that the obstructing substance absorbs into and/or adsorbs onto the object. The infiltration of the obstructing substance can reduce the amount of the treatment agent that can subsequently infiltrate into the object. The reduction of treatment agent infiltration can result in a reduction of residual treatment agent on a surface of the object after the treatment process.

The obstructing substance can comprise a substance suitable to infiltrate into the object and reduce the absorptive and/or adsorptive capacity of the object. For example, the obstructing substance can comprise at least one of water, an alcohol, and a glycol. In various examples, the obstructing substance can comprise water. In various examples, the obstructing substance considerably excludes a treatment agent. As used herein "considerably excludes" is meant to mean at the obstructing substance has less than 10% treatment agent by weight such as, for example, less than 5% treatment agent, in some examples less than 1% treatment agent, in some examples less than 0.1% treatment agent, and in other examples has essentially no treatment agent by weight. The obstructing substance can comprise at least one of a liquid and a gas. For example, the obstructing substance can be a gaseous composition such as a vapor, a mist, a gas that has a temperature at least the critical temperature of the substance, or combinations thereof. In various examples, the obstructing substance can be any chemical that is general recognized as safe under 21 CFR Parts 20, 25, 170, 184, 186, and 570 (2016).

A method reduction of residuals of an object is provided herein. The method comprises contacting the object with the obstructing substance such that the object is infiltrated with at least a portion of the obstructing substance. The infiltration of the object by the obstructing substance can reduce the absorptive and/or adsorptive capacity of the object. In various examples, contacting the object with the obstructing substance can comprise at least one of spraying the obstructing substance in a liquid phase onto the object, vaporizing the obstructing substance and contacting the object with the vapor, generating a mist with the obstructing substance and contacting the object with the mist, contacting the object with a gas of the obstructing substance, soaking the object in a liquid comprising the obstructing substance, or depositing the obstructing substance on the object with another suitable means such as, for example, a cloth. In various examples, prior to contacting the object with the obstructing substance, the object can be pretreated such as, for example, the surface of the object may be wiped with, for example, a cloth to remove debris.

A temperature of the obstructing substance may be any temperature suitable to facilitate infiltration of the object. In certain aspects, the temperature of the obstructing substance can enhance the rate of infiltration of the obstructing substance into the object. The temperature of the obstructing substance can be maintained and/or adjusted by, for example, a heater, a dispenser, a vaporizer, and combinations thereof. The temperature of the obstructing substance can be in the range of 0 degrees Celsius to 200 degrees Celsius such as, for example, 10 degrees Celsius to 150 degrees Celsius, 30 degrees Celsius to 90 degrees Celsius, 50 degrees Celsius to 85 degrees Celsius, or 65 degrees Celsius to 85 degrees Celsius. In various examples, the temperature of the obstructing substance can be 75 degrees Celsius.

In various examples, the obstructing substance can contact the object in an environment with any suitable pressure. For example, the contacting of the object with obstructing substance can be at a pressure in a range of 0.1 Torr to 7600 Torr such as, for example, 0.2 Torr to 0.8 Torr, 760 to 7600 Torr, 760 to 2280 Torr, 1 Torr to 750 Torr, 10 Torr to 300 Torr, 10 Torr to 200 Torr, or 10 Torr to 100 Torr. In various examples, the pressure can be less than 750 Torr. All pressures herein refer to the absolute pressure unless otherwise indicated. The pressure of the environment and the temperature of the obstructing substance can be adjusted to provide the obstructing substance in a desired state, such as a liquid or gaseous composition.

The object can be contacted by the obstructing substance for a time period suitable to facilitate infiltration. The time period that the obstructing substance contacts the object can affect infiltration of the obstructing substance into the object. The contacting of the object with the obstructing substance can occur for a period of time ranging from 0.1 minutes to 120 minutes such as, for example, 0.1 minutes to 90 minutes, 0.1 minutes to 60 minutes, 0.1 minutes to 30 minutes, 0.1 minutes to 20 minutes, 0.1 minutes to 10 minutes, 0.5 minutes to 5 minutes, or 1 minute to 2 minutes. In various examples, it may be desirable to minimize the time period of contact with the obstructing substance such that the total time of a treatment process can be minimized.

The time period for contacting, the pressure of the environment, and/or the temperature of the obstructing substance can be selected based on the material employed to form the object. As known in the art, the type of material used to form the object affects the infiltration rate and absorptive and/or adsorptive capacity of the object. Thus, the time period for contacting, the pressure of the environment, and/or the temperature of the obstructing substance can be selected based on the material of the object in order to achieve infiltration of the obstructing substance into the object suitable to reduce the absorptive and/or adsorptive capacity of the object. In various examples, the object comprises at least one of metal, plastic, ceramic, and fabric. For example, the object can comprise a polymer such as at least one of polyamine, polyetherimide, polyvinyl chloride, polysulfone, polyetheretherketone, polymethylmethyacrylate, polyphenylene oxide, polyacetal, polycarbonate, and polyurethane. The object can comprise a medical device such as, for example, a scalpel, an endoscope, scissors, and the like.

After the object is infiltrated by the obstructing substance and the absorptive and/or adsorptive capacity of the object has been reduced, the object can be contacted with the treatment agent. In various examples, the contacting with the treatment agent can comprise at least one of spraying the treatment agent in a liquid phase onto the object, vaporizing the treatment agent and contacting the object with the vapor, generating a mist with the treatment agent and contacting the object with the mist, contacting the object with a gas of the treatment agent, soaking the object in a liquid comprising the treatment agent, or depositing the treatment agent on the object with another suitable means such as, for example, a cloth.

The treatment agent can comprise at least one of a cleaning agent, a disinfectant, and a sterilant. The treatment agent can comprise at least one of a liquid and a gas. For example, the obstructing substance can be a gaseous composition such as a vapor, a mist, or a gas. The treatment agent can comprise at least one of hydrogen peroxide, ethylene oxide, nitrogen oxide, ozone, glutaraldehyde, formaldehyde, peracetic acid, chlorine, iodine, and sodium hydroxide. In various examples, the treatment agent can comprise at least 10 percent by weight hydrogen peroxide such as, for example, at least 20 percent by weight, at least 30 percent by weight, at least 40 percent by weight, at least 50 percent by weight, at least 60 percent by weight, or at least 70 percent by weight hydrogen peroxide. In various examples, the treatment agent comprises hydrogen peroxide and a balance of water. In various examples, the treatment agent can comprise hydrogen peroxide vapor.

A temperature of the treatment agent can be suitable to at least substantially remove the bioburden from the object. In various examples, the temperature of the treatment agent can reduce infiltration of the treatment agent into the object. The temperature of the treatment agent can be maintained and/or adjusted by, for example, a heater, a dispenser, a vaporizer, and combinations thereof. The temperature of the treatment agent can be in the range of 0 degrees Celsius to 200 degrees Celsius such as, for example, 25 degrees Celsius to 80 degrees Celsius, 40 degrees Celsius to 70 degrees Celsius, or 40 degrees Celsius to 65 degrees Celsius. The temperature of the obstructing substance and the temperature of the treatment agent can be the same or different.

In various examples, the treatment agent can contact the object in an environment with any suitable pressure. For example, the contacting of the object with treatment agent can be at a pressure in a range of 0.1 Torr to 7600 Torr such as, for example, 0.2 Torr to 0.8 Torr, 760 to 7600 Torr, 760 to 2280 Torr, 1 Torr to 750 Torr, 10 Torr to 300 Torr, 10 Torr to 200 Torr, or 10 Torr to 100 Torr. In various examples, the pressure can be less than 750 Torr. The pressure of the environment and the temperature of the treatment agent can be adjusted to provide the treatment agent in the desired state such as, a liquid or gaseous composition.

The object may be contacted by the treatment agent for a time period suitable to at least substantially remove bioburden from the object. The time period that the treatment agent contacts the object can affect the removal of bioburden from the object and may be adjusted to achieve the desired level of removal. The time period can be in a range from 1 minute to 120 minutes such as, for example, 1 minute to 90 minutes, 10 minutes to 70 minutes, 10 minutes to 60 minutes, 10 minutes to 50 minutes, 10 minutes to 40 minutes, 10 minutes to 30 minutes, or 10 minutes to 20 minutes. The time period of contact for the obstructing substance with the object and the time period for contact of the treatment agent with the object can be the same or different.

The treatment agent can be removed from the object following treatment. The removal of the treatment agent may be enhanced by infiltrating the object with the obstructing substance such that the absorptive and/or adsorptive capacity of the object can be reduced prior to treating the object with the treatment agent. For example, there may be less treatment agent that penetrates the object or is present on a surface of the object when the object has been contacted with the obstructing substance prior to the treatment agent as compared to a surface of an object that has not been contacted with obstructing substance prior to the treatment agent. Removing the treatment agent from the object can comprise at least one of generating a plasma and contacting the treatment agent with the plasma, exposing the object to an environment having a pressure less than 1 atmosphere absolute, contacting the object with a gas (e.g., air drying), rinsing the object with a solution (e.g., water), and wiping the object (e.g., a cloth). In various examples, the removal process alone may only remove the bulk hydrogen peroxide and may not remove residual hydrogen peroxide.

Exposing the object to an environment having a pressure less than 1 atmosphere absolute can facilitate the removal of the treatment agent of the object. Reducing the pressure of the environment the object is exposed to can include removing gas from a chamber the object is disposed within. The reduced pressure the object is exposed to can be 0.1 Torr to 750 Torr, such as, for example, 0.2 Torr to 0.8 Torr, 10 Torr to 300 Torr, 10 Torr to 200 Torr, or 10 Torr to 100 Torr. In various examples, the reduced pressure is less than 750 Torr. After exposing the object to the reduced pressure, the chamber can be allowed to return to atmospheric pressure.

After removal of the treatment agent from the object, the object can be ready for the next use and in various examples can have at least a substantially reduced bioburden. The residual treatment agent on a surface the object may be reduced due to the contacting with the obstructing substance prior to the treatment agent. For example, a residual content of the treatment agent on a surface of the object can be less than or equal to 1,500 parts per million of treatment agent by weight per square centimeter of surface area of the object by weight (ppm/cm$^2$) such as, for example, less than or equal to 1,000 ppm/cm$^2$ by weight, less than or equal to 700 ppm/cm$^2$ by weight, less than or equal to 600 ppm/cm$^2$ by weight, less than or equal to 500 ppm/cm$^2$ by weight, or less than or equal to 400 ppm/cm$^2$ by weight.

Referring to the FIGURE, an apparatus 100 reduction of residuals is provided. The apparatus 100 comprises a chamber 102 and a dispenser 116. The chamber 102 can be suitable to receive an object 104 and can be suitable to subject the object 104 to a treatment process. The dispenser 116 can be in fluid communication with the chamber 102 and can provide obstructing substance and treatment agent to the chamber 102 as a liquid or as a gaseous composition. In various examples, the dispenser 116 can comprise a vaporizer suitable to vaporize the obstructing substance and/or treatment agent into a vapor and provide the vapor the chamber 102. The vaporizer can be suitable to provide the vapor to the chamber 102 at the temperatures set forth herein, such as at a temperature in a range of 0 degrees Celsius to 200 degrees Celsius. In various examples, a valve 108 can be located between the dispenser 116 and the chamber 102 to control communication between the dispenser 116 and the chamber 102.

In various examples, the apparatus 100 can comprise a second dispenser (not shown) in fluid communication with the chamber 102 to provide at least one of the treatment agent and the obstructing substance to the chamber 102. In certain examples, the first dispenser 116 provides the obstructing substance to the chamber 102 and the second disperser provides the treatment agent to the chamber 102. The quantity and configuration of the dispensers is for illustration purposes only and there may be a different quantity or configuration of dispensers.

The chamber 102 can receive the obstructing substance and the treatment agent from the dispenser 116. The chamber 102 can be suitable and operate under suitable conditions and parameters to facilitate infiltration of at least a portion of the obstructing substance into the object 104. The chamber 102 can be suitable to contact the object 104 with the treatment agent after the infiltration of the at least portion of the obstructing substance into the object 104. For example, the chamber 102 can be suitable to receive the obstructing substance from the dispenser 116 (or a second dispenser) to the object 104. The chamber 102 can be sealable such that the obstructing substance and the treatment agent can be sealably contained within the chamber 102.

In various examples, the apparatus 100 can comprise a vacuum pump 112, a vent valve 110, and a radio frequency (RF) generator 114. The vacuum pump 112 and the vent valve 110 can be in fluid communication with the chamber 102. The vacuum pump 112 and the vent valve 110 can be suitable to control a pressure of the chamber 102. For example, the vent valve 110 in an open state can enable communication between the chamber 102 and an environment 120 outside of the chamber 102 via a filter 118 such that the pressure in the chamber 102 may equalize to the pressure of the environment 120. The vent valve 110 in the closed state can prevent communication between the chamber 102 and the environment 120 to increase or decrease the pressure in the chamber relative to the pressure of the environment 120.

The RF generator 114 can be in communication with the chamber 102 and can generate a plasma utilizing RF energy. The term "plasma" is intended to include any portion of the gas or vapor that contains electrons, ions, free radicals, dissociated and/or excited atoms, and/or molecules produced as a result of an applied electric field, including any accompanying radiation that might be produced.

The chamber 102 can be suitable to facilitate removal of the treatment agent from the object 104. For example, the chamber 102, as supported by the RF generator 114, can be suitable to generate a plasma and the chamber 102 can be suitable to contact the plasma with the treatment agent. The plasma can be initiated by applying RF energy from RF generator 114. In the plasma, bulk treatment agent can be disassociated into reactive species that collide/react with and reduce and/or eliminate bioburden. In various examples, the plasma can convert bulk hydrogen peroxide into water and oxygen. The plasma can be maintained for a sufficient time to achieve treatment such as, for example, disinfection and/or sterilization of the object 104. In general, plasma can be used to remove bulk treatment agent and can enhance sterilization efficacy.

The chamber 102, as supported by the vacuum pump 112, can be suitable to expose the object 104 to an environment having a pressure less than 1 atmosphere absolute. For example, the vacuum pump 112 can remove gas from the chamber 102 in order to reduce the pressure in the chamber 102. The reduced pressure can lower the boiling point of the treatment agent and facilitate the evaporation of the treatment agent. Upon evaporation, the treatment agent departs the object 104 and can leave the chamber 102 via the vacuum pump 112. In various examples, a valve 106 can be disposed between the vacuum pump 112 and the chamber 102 in order to control the removal of gas from the chamber 102.

The chamber 102, supported by the vacuum pump 112 and the vent valve 110, can contact the object with a gas (e.g., air wash). For example, the vacuum pump 112 can reduce the pressure in the chamber 102 by removing gas from the chamber 102. The vent valve 110 can be in an open state to enable communication between the chamber 102 and the environment 120 such that gas can enter the chamber 102 and increase the pressure in the chamber 102. The gas that enters the chamber 102 can facilitate the removal of the treatment agent from the object 104.

The chamber 102, supported by the dispenser 116 can rinse the object with a solution (e.g., water). For example, the dispenser 116 can provide the solution to the chamber 102 as a liquid or as a gaseous composition. The solution can contact the object 104 and facilitate removal of the treatment agent from the object 104. In various examples, the chamber 102 can be suitable to wipe the object automatically.

EXAMPLES

The present disclosure will be more fully understood by reference to the following example, which provides illustrative non-limiting aspects of the invention. The example describes treatment processes used to clean, disinfect, and/or sterilize objects.

Example

Coupons 1-3 comprised of polyurethane were subjected to treatment processes A-B. Each treatment process A-B included a STERRAD® sterilization process and treatment process B included a residual removal process. For each treatment process A-B, coupons 1-3 were placed in a STERRAD® sterilizer manufactured by Advanced Sterilization Products, of Irvine, California, a division of Ethicon, Inc. of Somerville, New Jersey. The sterilization chamber of the sterilizer was sealed and the sterilization process was initialized. The sterilization process comprised a step (i) of a plasma pretreatment including generating a plasma and contacting the plasma with the coupons 1-3. A step (ii) included contacting the coupons 1-3 with a treatment agent vapor of 59% by weight hydrogen peroxide at 47 degrees Celsius. The treatment agent vapor was contacted with the coupons for 15.5 minutes in order to allow the treatment agent vapor to at least substantially reduce bioburden from the coupons 1-3. During step (ii), the pressure in the sterilization chamber was reduced to a pressure in a range of 0.2 Torr to 0.8 Torr. A step (iii) comprised venting the sterilization chamber to atmosphere and increasing the pressure in the sterilization pressure to the environmental pressure in the room. A step (iv) included a plasma post treatment including generating a plasma and contacting the plasma with the coupons 1-3 for 2 minutes. The plasma post treatment removed bulk hydrogen peroxide from the coupons 1-3 and converted the bulk hydrogen peroxide into water and oxygen. For each sterilization process, the steps (i)-(iv) were repeated such that each step (i)-(iv) was performed twice.

In treatment process B, the coupons 1-3 were treated similarly to treatment process A, except that before the sterilization process, the coupons 1-3 were contacted with an obstructing substance of water vapor in a temperature range of 75 degrees Celsius to 85 degrees Celsius by vaporizing water into the sterilization chamber. The water vapor was contacted with the coupons 1-3 for 5 minute in order to allow at least a portion of the water vapor to infiltrate the coupons 1-3.

After each treatment process A-B, coupons 1-3 were tested to determine the residual content of hydrogen peroxide on each coupon 1-3 via spectroscopy. In order to determine the residual content of the hydrogen peroxide, coupons 1-3 were individually extracted. The extract was contacted with aqueous titanium (IV) reagent. The titanium (IV) reagent reacted with residual hydrogen peroxide of the coupons 1-3 and developed a colored complex with an absorbance at 410 nm. The absorbance of each titanium (IV) reagent was measured at 410 nm and a residual content of hydrogen peroxide for each coupon 1-3 was calculated based on the surface area of each coupon in ppm/cm$^2$. Three measurements for each coupon 1-3 were made and the results for treatment processes A-B are shown in Table 1.

TABLE 1

Residual hydrogen peroxide after treatment (ppm/cm$^2$)

| Coupon | Treatment Process | |
|---|---|---|
| | A | B |
| 1 | 784 | 717 |
| | 786 | 717 |
| | 786 | 719 |
| 2 | 1030 | 960 |
| | 1029 | 956 |
| | 1031 | 961 |
| 3 | 1260 | 695 |
| | 1258 | 692 |
| | 1258 | 697 |

Coupons 1-3 had less residual hydrogen peroxide after treatment process B than after treatment process A. Coupon 1 had, on average, 9% less residual hydrogen peroxide after the sterilization process according to treatment process B than after the sterilization process according to treatment process A. Coupon 2 had, on average, 7% less residual hydrogen peroxide after the sterilization process according to treatment process B than after the sterilization process according to treatment process A. Coupon 3 had, on average, 45% less residual hydrogen peroxide after the sterilization process according to treatment process B than after the sterilization process according to treatment process A. The reduced residual content of hydrogen peroxide in treatment process B showed that the absorptive and/or adsorptive capacity of the coupons 1-3 had been reduced by the contact with the water vapor in treatment process B such that the infiltration of the object with the hydrogen peroxide was limited.

The grammatical articles "a", "an", and "the", as used herein, are intended to include "at least one" or "one or more", unless otherwise indicated, even if "at least one" or "one or more" is expressly used in certain instances. Thus, the articles are used herein to refer to one or more than one (i.e., to "at least one") of the grammatical objects of the article. Further, the use of a singular noun includes the plural, and the use of a plural noun includes the singular, unless the context of the usage requires otherwise.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although various examples have been described herein, many modifications, variations, substitutions, changes, and equivalents to those examples may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed examples. The following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the invention according to the present disclosure include, but are not limited to, the aspects listed in the following numbered clauses.

1. A method for reduction of residuals comprising:
   contacting an object with an obstructing substance such that the object is infiltrated with at least a portion of the obstructing substance, wherein a capacity of the object is reduced by the obstructing substance, the capacity selected from at least one of absorptive and adsorptive capacity; and
   contacting the object with a treatment agent after the capacity of the object is reduced, wherein infiltration of the object with the treatment agent is limited by the reduction of the capacity of the object.
2. The method of clause 1, further comprising disinfecting the object with the treatment agent.
3. The method of any one of clauses 1-2, wherein the obstructing substance comprises at least one of water, alcohol, and a glycol.
4. The method of any one of clauses 1-3, wherein the obstructing substance is at least one of a liquid, a mist, a vapor, and a gas.
5. The method of any one of clauses 1-4, wherein the obstructing substance comprises water vapor.
6. The method of any one of clauses 1-5, wherein the treatment agent comprises at least one of a cleaning agent, a disinfectant, and a sterliant.
7. The method of any one of clauses 1-6, wherein the treatment agent comprises at least one of hydrogen peroxide, ethylene oxide, nitrogen oxide, ozone, glutaraldehyde, formaldehyde, peracetic acid, chlorine, iodine, and sodium hydroxide.
8. The method of any one of clauses 1-7, wherein the treatment agent comprises at least one of a liquid, a mist, a vapor, and a gas.
9. The method of any one of clauses 1-8, wherein the treatment agent comprises hydrogen peroxide vapor.

10. The method of any one of clauses 1-9, further comprising removing the treatment agent from the object.
11. The method of clause 10, wherein removing the treatment agent from the object comprises at least one of:
   generating a plasma and contacting the treatment agent with the plasma;
   exposing the object to an environment having a pressure less than 1 atmosphere absolute;
   contacting the object with a gas;
   rinsing the object with a solution; and
   wiping the object.
12. The method of any one of clauses 10-11, wherein after removal of the treatment agent from the object, a residual content of the treatment agent on a surface of the object is less than or equal to 1,500 ppm/cm$^2$ by weight.
13. The method of any one of clauses 10-11, wherein after removal of the treatment agent from the object, a residual content of the treatment agent on a surface of the object is less than or equal to 1,000 ppm/cm$^2$ by weight.
14. The method of any one of clauses 1-13, wherein contacting the object with the obstructing substance occurs for a time in a range of 0.1 minutes to 120 minutes.
15. The method of any one of clauses 1-13, wherein contacting the object with the obstructing substance occurs for a time in a range of 0.1 to 10 minutes.
16. The method of any one of clauses 1-15, wherein contacting the object with the treatment agent occurs for a time in a range of 1 minute to 120 minutes.
17. The method of any one of clauses 1-16, wherein the obstructing substance has a temperature in a range of 0 degrees to 200 degrees Celsius.
18. The method of any one of clauses 1-16, wherein the obstructing substance has a temperature in a range of 30 degrees to 90 degrees Celsius.
19. The method of any one of clauses 1-18, wherein the object comprises at least one of polyamine, polyetherimide, polyvinyl chloride, polysulfone, polyetheretherketone, polymethylmethyacrylate, polyphenylene oxide, polyacetal, polycarbonate, and polyurethane.
20. A method for reduction of residuals comprising:
   contacting an object with a gaseous water composition such that the object is infiltrated with at least a portion of the gaseous water composition, wherein a capacity of the object is reduced by the gaseous water composition, the capacity selected from at least one of absorptive and adsorptive capacity;
   contacting the object with a gaseous hydrogen peroxide composition after the capacity of the object is reduced and disinfecting the object, wherein infiltration of the object with the gaseous hydrogen peroxide composition is limited by the reduction of the capacity of the object; and
   removing at least a portion of the gaseous hydrogen peroxide composition from the object, wherein after the removal of the gaseous hydrogen peroxide composition from the object, a residual content of the gaseous hydrogen peroxide composition remaining on a surface of the object is less than or equal to 1,500 ppm/cm$^2$ by weight.
21. The method of clause 20, wherein the gaseous water composition comprises water vapor.
22. The method of any one of clauses 20 to 21, wherein the gaseous hydrogen peroxide composition comprises hydrogen peroxide vapor.
23. An apparatus for reduction of residuals, comprising:
   a chamber suitable to receive an object;
   a dispenser in fluid communication with the chamber and the dispenser suitable to provide an obstructing substance and a treatment agent to the chamber; and
   the chamber suitable to facilitate infiltration of the obstructing substance into the object and suitable to contact the object with the treatment agent after the infiltration of the at least portion of the obstructing substance, wherein after removal of at least a portion of the treatment agent from the object, a residual content of the treatment agent remaining on the object is less than or equal to 1,500 ppm/cm$^2$ by weight.
24. The apparatus of clause 23, further comprising a second dispenser in fluid communication with the chamber suitable to provide at least one of the treatment agent and the obstructing substance.
25. The apparatus of any one of clauses 23-24, wherein the dispenser further comprises a vaporizer suitable to convert at least one of the obstructing substance and the treatment agent into a vapor and the dispenser suitable to provide the vapor to the chamber.
26. The apparatus of clause 25, wherein the vaporizer is suitable to provide the vapor at a temperature in a range of 0 degrees to 200 degrees Celsius.
27. The apparatus of any one of clauses 23-26, further comprising a radio frequency generator suitable to convert at least one of a select portion of the obstructing substance and a select portion of the treatment agent into a plasma.
28. The apparatus of any one of clauses 23-27, further comprising a pump in fluid communication with the chamber and the pump suitable to remove gas from the chamber.
29. The apparatus of any one of clauses 23-28, further comprising a valve in fluid communication with the chamber and suitable to transport gas into the chamber.
30. The apparatus of any one of clauses 23-29, wherein after the removal of at least a portion of the treatment agent from the object, a residual content of the treatment agent remaining on surface of the object is less than or equal to 1,000 ppm/cm$^2$ by weight.
31. The apparatus of any one of clauses 23-30, wherein the obstructing substance comprises at least one of water, an alcohol, and a glycol.
32. The apparatus of any one of clauses 23-31, wherein the treatment agent comprises at least one of hydrogen peroxide, ethylene oxide, nitrogen oxide, ozone, glutaraldehyde, formaldehyde, peracetic acid, chlorine, iodine, and sodium hydroxide.

In summary, numerous benefits have been described which result from employing the concepts described herein. The foregoing description of the one or more examples has been presented for purposes of illustration and description. It is not intended to be exhaustive or limiting to the precise form disclosed. Modifications or variations are possible in light of the above teachings. The one or more examples were chosen and described in order to illustrate principles and practical application to thereby enable one of ordinary skill in the art to utilize the various examples and with various modifications as are suited to the particular use contemplated. It is intended that the claims submitted herewith define the overall scope.

While the present disclosure provides descriptions of various specific aspects for the purpose of illustrating various aspects of the present disclosure and/or its potential applications, it is understood that variations and modifications will occur to those skilled in the art. Accordingly, the invention or inventions described herein should be understood to be at least as broad as they are claimed, and not as more narrowly defined by particular illustrative aspects provided herein.

What is claimed is:

1. A method for reduction of residuals comprising:
contacting an object comprising a polymer with a water composition, such that the object is infiltrated with at least a portion of the water composition, wherein a capacity of the object is reduced by the water composition, the capacity selected from at least one of absorptive and adsorptive capacity; and
contacting the object with a hydrogen peroxide composition that is separate from the water composition, wherein infiltration of the object with the hydrogen peroxide composition is limited by the reduction of the capacity of the object; and
removing at least a portion of the hydrogen peroxide composition from the object, wherein after the removal of the hydrogen peroxide from the object, a first residual content of the hydrogen peroxide remaining on a surface of the object is less than a second residual content of the hydrogen peroxide remaining on the surface of the object if the object was not contacted with the water composition prior to contacting the object with the hydrogen peroxide.

2. The method of claim 1, further comprising disinfecting the object with the hydrogen peroxide composition.

3. The method of claim 1, wherein the hydrogen peroxide composition comprises at least one of a liquid, a mist, a vapor, and a gas.

4. The method of claim 1, wherein removing the hydrogen peroxide composition from the object comprises at least one of:
generating a plasma and contacting the hydrogen peroxide composition with the plasma;
exposing the object to an environment having a pressure less than 1 atmosphere absolute;
contacting the object with a gas;
rinsing the object with a solution; and
wiping the object.

5. The method of claim 1, wherein after removal of the hydrogen peroxide composition from the object, a residual content of the hydrogen peroxide on a surface of the object is less than or equal to 1,500 ppm/cm2 by weight.

6. The method of claim 1, wherein after removal of the hydrogen peroxide from the object, a residual content of the hydrogen peroxide on a surface of the object is less than or equal to 1,000 ppm/cm2 by weight.

7. The method of claim 1, wherein contacting the object with the water composition occurs for a time in a range of 0.1 minutes to 120 minutes.

8. The method of claim 1, wherein contacting the object with the hydrogen peroxide composition occurs for a time in a range of 1 minute to 120 minutes.

9. The method of claim 1, wherein the water composition has a temperature in a range of 0 degrees to 200 degrees Celsius.

10. The method of claim 1, wherein the water composition has a temperature in a range of 30 degrees to 90 degrees Celsius.

11. The method of claim 1, wherein the object comprises at least one of polyamine, polyetherimide, polyvinyl chloride, polysulfone, polyetheretherketone, polymethylmethacrylate, polyphenylene oxide, polyacetal, polycarbonate, and polyurethane.

12. The method of claim 1, wherein the hydrogen peroxide composition comprises hydrogen peroxide vapor.

13. The method of claim 1, wherein after the removal of the hydrogen peroxide composition from the object, the first residual content of the hydrogen remaining on the surface of the object is at least 7% less and no more than 45% less than the second residual content of the hydrogen peroxide composition remaining on the surface of the object if the object was not contacted with the water composition prior to contacting the object with the hydrogen peroxide.

14. The method of claim 1, wherein contacting the object with the water composition occurs for a time in a range of 0.5 minutes to 120 minutes, and wherein contacting the object with the hydrogen peroxide composition occurs for a time in a range of 10 minute to 70 minutes.

15. The method of claim 14, wherein the water composition has a temperature in a range of 30 degrees to 90 degrees Celsius and wherein the hydrogen peroxide composition has a temperature in a range of 25 degrees to 80 degrees Celsius.

16. The method of claim 15, wherein the water composition is contacted with the object at a pressure of less than 750 Torr and the hydrogen peroxide composition is contacted with the object at a pressure of less than 750 Torr.

17. The method of claim 16, wherein removing the hydrogen peroxide composition from the object comprises generating a plasma and contacting the hydrogen peroxide composition with the plasma.

18. The method of claim 1, wherein the residual content of the hydrogen peroxide is determined by extracting the surface of the object, contacting the extract from the surface with titanium (IV) reagent to form a test solution, and measuring an absorbance of the test solution at 410 nm via spectroscopy.

19. The method of claim 1, wherein contacting the object with the water composition is performed by a dispenser, and contacting the object with a hydrogen peroxide composition that is separate from the water composition is performed by the dispenser.

20. The method of claim 1, wherein contacting the object with the water composition is performed by a first dispenser, and contacting the object with a hydrogen peroxide composition that is separate from the water composition is performed by a second dispenser.

21. A method for reduction of residuals comprising:
contacting an object with a gaseous water composition, wherein the gaseous water composition comprises a liquid or a mist, such that the object is infiltrated with at least a portion of the gaseous water composition, wherein a capacity of the object is reduced by the gaseous water composition, the capacity selected from at least one of absorptive and adsorptive capacity;
contacting the object with a gaseous hydrogen peroxide composition that is separate from the gaseous water composition to disinfect the object, wherein infiltration of the object with the gaseous hydrogen peroxide composition is limited by the reduction of the capacity of the object; and
removing at least a portion of the gaseous hydrogen peroxide composition from the object, wherein after the removal of the gaseous hydrogen peroxide composition from the object, a residual content of the gaseous hydrogen peroxide composition remaining on a surface of the object is less than or equal to 1,500 ppm/cm2 by weight.

22. The method of claim 21, wherein the gaseous water composition comprises water vapor.

23. The method of claim 21, wherein the gaseous hydrogen peroxide composition comprises hydrogen peroxide vapor.

24. A method for reduction of residuals comprising:
contacting an object with a water composition, such that the object is infiltrated with at least a portion of the water composition, wherein a capacity of the object is reduced by the water composition, the capacity selected from at least one of absorptive and adsorptive capacity; and
contacting the object with a hydrogen peroxide vapor that is separate from the water composition, wherein infiltration of the object with the hydrogen peroxide vapor is limited by the reduction of the capacity of the object; and
removing at least a portion of the hydrogen peroxide vapor from the object, wherein after the removal of the hydrogen peroxide from the object, a first residual content of the hydrogen peroxide remaining on a surface of the object is less than a second residual content of the hydrogen peroxide remaining on the surface of the object if the object was not contacted with the water composition prior to contacting the object with the hydrogen peroxide.

* * * * *